US009468478B2

(12) United States Patent
Boraiah (10) Patent No.: US 9,468,478 B2
(45) Date of Patent: Oct. 18, 2016

(54) INTERLOCKING INTRAMEDULLARY ROD ASSEMBLY FOR PROXIMAL FEMORAL FRACTURES, INCLUDING UNSTABLE HIP FRACTURES

(71) Applicant: Sreevathsa Boraiah, Lake Grove, NY (US)

(72) Inventor: Sreevathsa Boraiah, Lake Grove, NY (US)

( * ) Notice: Subject to any disclaimer, the term of this patent is extended or adjusted under 35 U.S.C. 154(b) by 0 days.

(21) Appl. No.: 14/340,235

(22) Filed: Jul. 24, 2014

(65) Prior Publication Data

US 2015/0032110 A1   Jan. 29, 2015

Related U.S. Application Data

(60) Provisional application No. 61/958,281, filed on Jul. 24, 2013.

(51) Int. Cl.
*A61B 17/72* (2006.01)
*A61B 17/74* (2006.01)

(52) U.S. Cl.
CPC ........... *A61B 17/725* (2013.01); *A61B 17/744* (2013.01)

(58) Field of Classification Search
CPC ............ A61B 17/744; A61B 17/1631; A61B 17/7208; A61B 17/72; A61B 17/80; A61B 17/8625; A61B 17/866; A61B 17/7225; A61B 17/7233; A61B 17/7241; A61B 17/8052; A61B 17/864; A61B 17/8872; A61B 17/92; A61B 17/1725; A61B 2017/00831; A61B 19/54
USPC ................ 606/62–68, 70, 301–308, 282, 88
See application file for complete search history.

(56) References Cited

U.S. PATENT DOCUMENTS

| | | | |
|---|---|---|---|
| 7,824,419 B2 | 11/2010 | Boraiah | |
| 8,109,943 B2 | 2/2012 | Boraiah et al. | |
| 2002/0107578 A1* | 8/2002 | Speitling | A61B 17/7233 623/23.6 |
| 2007/0049940 A1* | 3/2007 | Wallace | A61B 17/72 606/62 |
| 2007/0213757 A1 | 9/2007 | Boraiah | |
| 2009/0048600 A1 | 2/2009 | Matityahu et al. | |
| 2010/0262166 A1 | 10/2010 | Boraiah et al. | |
| 2011/0196370 A1* | 8/2011 | Mikhail | A61B 17/72 606/62 |
| 2012/0265202 A1 | 10/2012 | Schwammberger et al. | |
| 2014/0330274 A1* | 11/2014 | Matityahu | A61B 17/744 606/64 |

OTHER PUBLICATIONS

Haidukewych et al., Reverse Obliquity Fractures of the Intertrochanteric Region of the Femur, The Journal of Bone and Joint Surgery, 2001, vol. 83-A, No. 5, pp. 643-650.
Kregor et al., Unstable Pertrochanteric Femoral Fractures, Journal of Orthopaedic Trauma, 2005, vol. 19, No. 1, pp. 63-66.

* cited by examiner

*Primary Examiner* — Pedro Philogene
(74) *Attorney, Agent, or Firm* — Pandiscio & Pandiscio (57) ABSTRACT

An interlocking intramedullary rod assembly for treating a fracture, the assembly including an intramedullary rod having a distal section and a proximal section; a distal interlocking screw; and a proximal interlocking screw; wherein the distal section comprises a static distal seat for receiving the distal interlocking screw, and the proximal section comprises a dynamic proximal seat for receiving the proximal interlocking screw; and further wherein the static distal seat is configured to secure the distal interlocking screw to the intramedullary rod such that the distal interlocking screw cannot move relative to the intramedullary rod, and the dynamic proximal seat is configured to secure the proximal interlocking screw to the interlocking rod such that a first end of the proximal interlocking screw cannot move relative to the intramedullary rod and the second end of the proximal interlocking screw can move relative to the intramedullary rod.

18 Claims, 6 Drawing Sheets

INTERLOCKING INTRAMEDULLARY ROD ASSEMBLY FOR PROXIMAL FEMORAL FRACTURES, INCLUDING UNSTABLE HIP FRACTURES

REFERENCE TO PENDING PRIOR PATENT APPLICATION

This patent application claims benefit of pending prior U.S. Provisional Patent Application Ser. No. 61/958,281, filed Jul. 24, 2013 by Sreevathsa Boraiah for TENSION BAND NAIL: FOR PROXIMAL FRACTURES INCLUDING UNSTABLE HIP FRACTURES, which patent application is hereby incorporated herein by reference.

FIELD OF THE INVENTION

The present invention relates generally to an interlocking intramedullary rod assembly for treatment of fractures of a long bone, and more particularly to an interlocking intramedullary rod assembly for treating proximal femoral fractures including unstable hip fractures. The interlocking intramedullary rod assembly can also be utilized in other applications in the body where the biomechanical principals of tension banding apply. The interlocking intramedullary rod assembly can also be used in situations where a fracture is to be at least partially reduced after introduction of the intramedullary rod, with fracture reduction being effected either by the surgeon or as a result of weight bearing. Even more particularly, the present invention relates to a load-bearing interlocking intramedullary rod assembly which comprises an intramedullary rod which is inserted into the intramedullary canal of a fractured proximal femur for treatment of a proximal femur fracture.

BACKGROUND OF THE INVENTION

Hip fractures present significant healthcare issues. These healthcare issues includes mortality, morbidity and increased healthcare costs. Improvements to the rate of reliable healing would significantly benefit patient health and reduce healthcare costs.

Proximal fractures of the femur are traditionally treated with either (i) an intramedullary rod (sometimes referred to as an intramedullary nail) which is positioned in the intramedullary canal of the femur, or (ii) a plate applied to the side of the femur and fixed in place with one or more screws set into the femur. The choice of using an intramedullary rod or a plate and screw is generally based on the location and complexity of the fracture.

As noted above, the intramedullary rod is placed in the intramedullary canal of the femur and typically provides excellent mechanical stability for the bone. Among other things, the intramedullary rod exhibits good weight-sharing properties. However, the use of an intramedullary rod also involves a more complex surgical procedure and higher cost.

Plates such as the Dynamic Hip Screw (DHS) plate are generally simpler to deploy and less expensive than intramedullary rods. Plates generally work well for stable intertrochanteric fractures. However, in subtrochanteric fractures and unstable intertrochanteric fractures, it is difficult to achieve proper compression of the fracture site with plates upon the application of weight. Therefore, most subtrochanteric fractures and unstable intertrochanteric fractures are treated with intramedullary rods.

When the treatment of subtrochanteric fractures and unstable intertrochanteric fractures by intramedullary rods is unsuccessful, the fractures are typically treated with tension band plates (such as a tension band blade plate) which utilize the geometry of the femoral subtrochanteric region and the compressive forces imposed by the surrounding musculature. A tension band construct, by definition, utilizes tensile forces and converts them into compressive forces. At an advanced level, when a tension band blade plate is applied to the tension side of the femur and pressure is thereafter applied, the tension band blade plate converts the tension forces into compressive forces which can be used to stabilize the fracture. Tension band blade plates are known to be effective in treating proximal femoral fractures. However, installation of these tension band blade plates requires substantial technical skill and involves a more complex operation. Therefore, the use of tension band blade plates is generally not suited for index surgery (i.e., the first surgery performed after the occurrence of a fracture), and is best suited for revising failed fracture repairs.

It is believed that a device that can combine the mechanical advantages of intramedullary rods with the mechanical advantages of tension band blade plates would be extremely useful for treating all kinds of proximal femoral fractures, including not only the aforementioned subtrochanteric fractures and unstable intertrochanteric fractures, but also including stable intertrochanteric fractures and other types of proximal femoral fractures. Such a device would also be extremely useful for treating fractures of other bones in the body. For the sake of clarity, even though the present invention may be used for all hip fractures (including stable and unstable intertrochanteric fractures, subtrochanteric fractures, and other types of proximal femoral fractures), and even though the present invention may be used for fractures of other bones in the body, the following discussion of the present invention will focus on subtrochanteric fractures and unstable intertrochanteric fractures.

Intramedullary rods have evolved over time. The first generation of intramedullary rods essentially involved inserting a solid rod down the intramedullary canal of the femur. This type of intramedullary rod is relatively primitive and only grossly aligns the bone. The first generation of intramedullary rods does not control motion at the fracture line in any specific plane.

The second generation of intramedullary rods was the dynamic interlocking intramedullary rod. The dynamic interlocking intramedullary rod allows for compression of the bone at the fracture site by allowing axial compression of the fracture. This axial compression of the fracture is achieved through the use of lag screws which pass through the bone, across the intramedullary rod and back into the bone. However, existing lag screw constructs do not control the coronal plane motion of the unstable and subtrochanteric fractures. Studies have shown that the dynamic interlocking intramedullary rod has not been as effective as desired. More particularly, for the repair of subtrochanteric fractures and fractures of the femoral neck or femoral head using a dynamic interlocking intramedullary rod, the intramedullary rod is driven into the femur from the proximal end and a femoral neck pin is introduced into the femoral head via the femoral neck of the femur, with the femoral neck pin passing through a bore formed in the intramedullary rod at an oblique angle to the axis of the intramedullary rod. The dynamic interlocking intramedullary rod, when placed under a load, is subjected to a combined stress which is composed of compressive and tensile stresses and shear loads. In the case of delayed healing and overload, a crack or fissure may develop in the bone, namely at the site at which the highest shear stress occurs. Current dynamic interlocking intramedullary rods do not provide any kind of unique biomechanical advantage for fracture healing in unstable intertrochanteric and subtrochanteric fractures except acting as an intramedullary buttress. The dynamic interlocking intramedullary rod does not offer any anatomic site-specific advantage for healing of the fracture.

The present invention addresses this biomechanical problem by reducing the shear loads on the intramedullary rod and provides a more stable biomechanical environment for a more accelerated and reliable healing of the fracture.

SUMMARY OF THE INVENTION

It is an object of the present invention to provide a novel interlocking intramedullary rod assembly for the treatment of a proximal femur fracture whereby the interlocking intramedullary rod assembly exhibits load bearing properties and creates a biomechanically-conducive environment for reliable fracture healing.

In one form of the present invention, the new interlocking intramedullary rod assembly comprises an intramedullary rod that is positioned in the intramedullary canal of the femur, a distal interlocking screw that locks the distal part of the intramedullary rod to the distal femur, and a proximal interlocking screw which secures the intramedullary rod to the proximal femur in a new and unique manner. More particularly, the intramedullary rod is placed in the intramedullary canal of the femur antegrade (i.e., distally from the proximal trochanter). The intramedullary rod has an approximately 12 degree bend at its proximal end to accommodate the natural geometry of the proximal femur. After the intramedullary rod has been placed in the intramedullary canal of the femur, the proximal interlocking screw is deployed. The proximal interlocking screw is a lag screw and is advanced from the lateral aspect of the femur through a dynamic proximal seat formed in the intramedullary rod and then into the femoral head. This dynamic proximal seat extends lateral-to-medial, and has a circular configuration on its medial end and a slot configuration on its lateral end. The dynamic proximal seat is referred to as a "dynamic" seat inasmuch as this seat allows for selected motion of the proximal interlocking screw relative to the intramedullary rod. The proximal interlocking screw is placed at an angle of approximately 124-127 degrees to the longitudinal axis of the intramedullary rod, based on the patient's anatomy. The angle between the intramedullary rod and the proximal interlocking screw is pre-selected by the surgeon after templating pre-operative radiographs. Note that this is a fixed angle for any given intramedullary rod and proximal interlocking screw combination. Therefore, the surgeon will select the appropriate intramedullary rod and proximal interlocking screw combination from inventory. After the proximal interlocking screw is deployed in the dynamic proximal seat, the distal interlocking screw is deployed in the distal part of the intramedullary rod. The distal interlocking screw is placed from the lateral side of the femur through a static distal seat in the intramedullary rod and into the medial side of the femur. The static distal seat in the distal part of the intramedullary rod extends lateral-to-distal and comprises a circular opening on its medial end and a circular opening on its lateral end. The static distal seat is referred to as a "static" seat inasmuch as this seat does not allow for motion of the distal interlocking screw relative to the intramedullary rod.

In accordance with the present invention, after the proximal interlocking screw is inserted into the dynamic proximal seat at an angle of between approximately 124-127 degrees to the longitudinal axis of the intramedullary rod, the surgeon may choose to further change the angle at which the proximal interlocking screw extends through the dynamic proximal seat (e.g., up to approximately 138 degrees) depending on the patient's anatomy, fracture configuration and the opposition of fracture fragments. Also, upon the application of weight (i.e., when the patient stands), the proximal interlocking screw shifts position within the dynamic proximal seat in order to allow a partial reduction of the fracture, e.g., within the given range of approximately 124-138 degrees. Angular locking means are provided for locking the proximal interlocking screw relative to the intramedullary rod. The proximal interlocking screw can be locked to the intramedullary rod at various stages of the procedure, e.g., (i) when the surgeon deems that the angle subtended at the insertion is good, or (ii) after the surgeon increases the valgus angle (if the surgeon deems that the option needs to exist to further increase the valgus angle after weight bearing, then the angular locking means are left open), or (iii) upon weight bearing, the fracture settles into its desired valgus, whereupon the proximal interlocking screw can be locked to the intramedullary rod.

In one preferred form of the invention, there is provided an interlocking intramedullary rod assembly for treating a fracture of a bone, said interlocking intramedullary rod assembly comprising:

an intramedullary rod comprising a distal section and a proximal section;

a distal interlocking screw; and a proximal interlocking screw;

wherein said distal section of said intramedullary rod comprises a static distal seat for receiving said distal interlocking screw, and said proximal section of said intramedullary rod comprises a dynamic proximal seat for receiving said proximal interlocking screw;

and further wherein said static distal seat is configured to secure said distal interlocking screw to said intramedullary rod such that said distal interlocking screw cannot move relative to said intramedullary rod, and said dynamic proximal seat is configured to secure said proximal interlocking screw to said interlocking rod such that a first end of said proximal interlocking screw cannot move relative to said intramedullary rod and the second end of said proximal interlocking screw can move relative to said intramedullary rod.

In another preferred form of the invention, there is provided a method for treating a fracture in the proximal femur, said method comprising:

providing an interlocking intramedullary rod assembly comprising:

an intramedullary rod comprising a distal section and a proximal section;

a distal interlocking screw; and a proximal interlocking screw;

wherein said distal section of said intramedullary rod comprises a static distal seat for receiving said distal interlocking screw, and said proximal section of said intramedullary rod comprises a dynamic proximal seat for receiving said proximal interlocking screw;

and further wherein said static distal seat is configured to secure said distal interlocking screw to said intramedullary rod such that said distal interlocking screw cannot move relative to said intramedullary rod, and said dynamic proximal seat is configured to secure said proximal interlocking screw to said interlocking rod such that a first end of said proximal interlocking screw cannot move relative to said intramedullary rod and the second end of said proximal interlocking screw can move relative to said intramedullary rod;

positioning said intramedullary rod in the intramedullary canal of the femur so that said distal section of said intramedullary rod resides within the shaft of the femur and said proximal section of said intramedullary rod resides within a proximal portion of the femur;

inserting said proximal interlocking screw through the proximal portion of the femur, through said dynamic proximal seat and into the proximal portion of the femur, and inserting said distal interlocking screw through the shaft of the femur, through said static distal seat and into the shaft of the femur; and adjusting the disposition of said proximal interlocking screw within said dynamic proximal seat so as to at least partially reduce the fracture.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The present invention comprises the provision and use of a novel interlocking intramedullary rod assembly for treating proximal femoral fractures and other fractures in the body.

Figure 1:
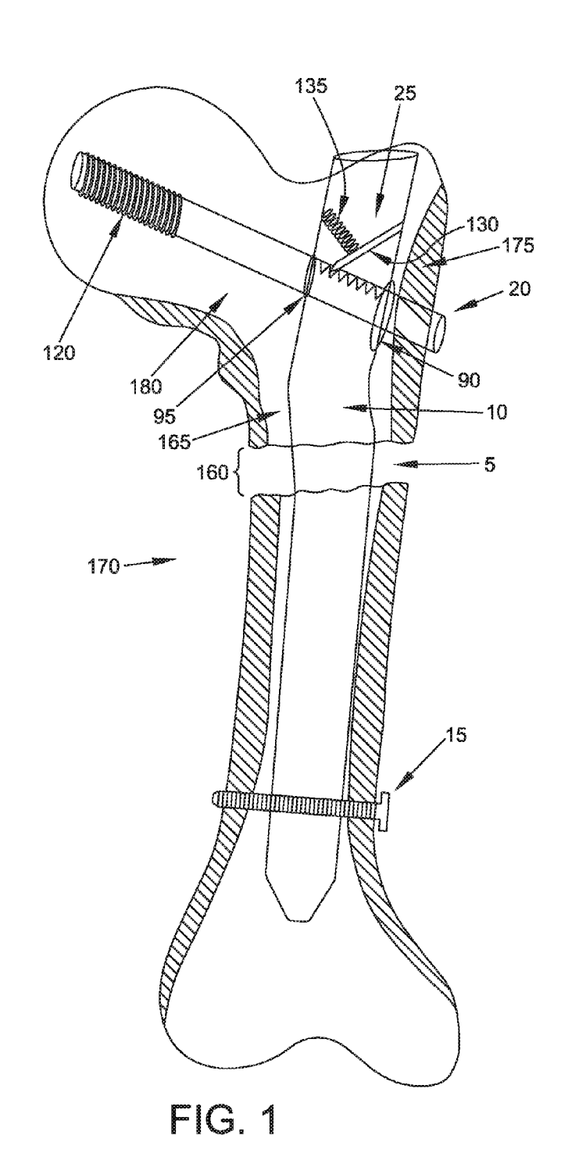
FIG. 1 is a schematic view showing a novel interlocking intramedullary rod assembly formed in accordance with the present invention, with the novel interlocking intramedullary rod assembly being disposed in a fractured femur, and with the interlocking intramedullary rod assembly and the fractured femur being shown prior to partial reduction of the fracture.

Looking first at FIG. 1, there is shown a novel interlocking intramedullary rod assembly 5 formed in accordance with the present invention. Novel interlocking intramedullary rod assembly 5 generally comprises an intramedullary rod 10, a distal interlocking screw 15, a proximal interlocking screw 20 and a locking finger 25 mounted to intramedullary rod 10 for selectively engaging proximal interlocking screw 20 as will hereinafter be discussed.

Intramedullary Rod

Figure 2:
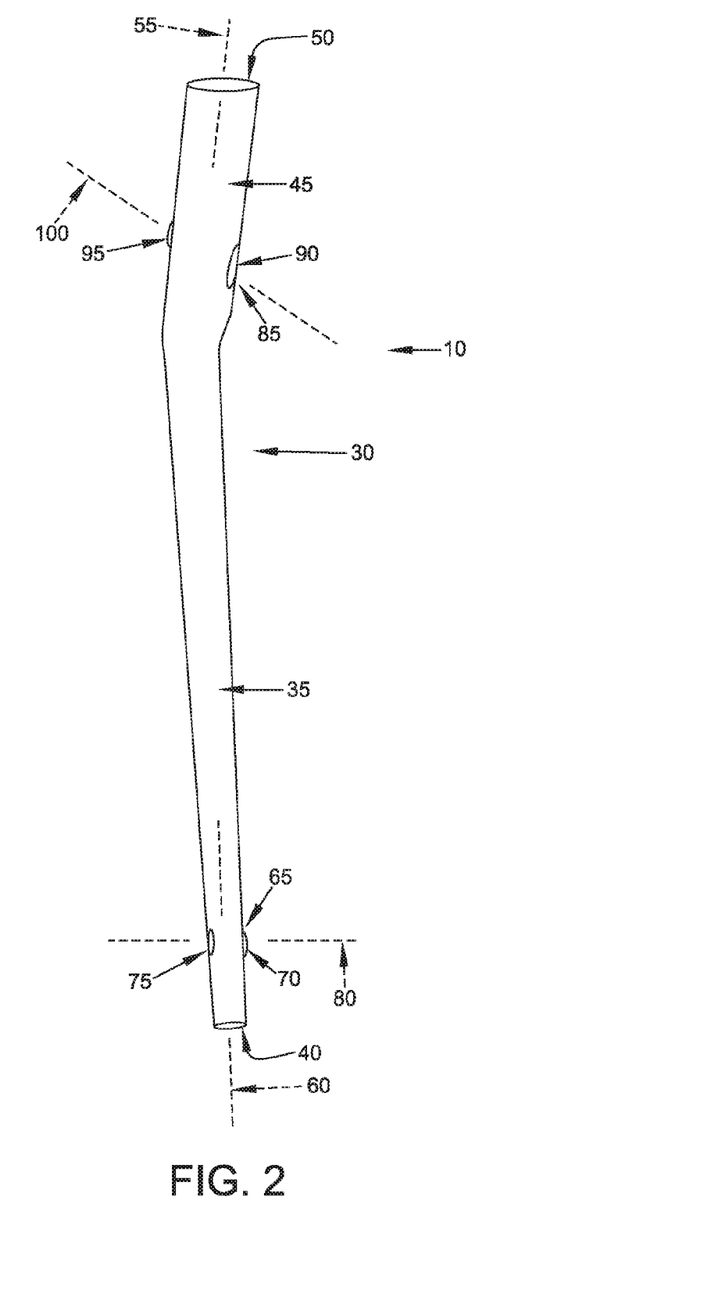
FIG. 2 is a schematic view showing the intramedullary rod of the novel interlocking intramedullary rod assembly of FIG. 1.

Looking now at FIGS. 1 and 2, intramedullary rod 10 generally comprises a shaft 30 having a distal section 35 terminating in a distal end 40 and a proximal section 45 terminating in a proximal end 50. Distal section 35 and proximal section 45 are formed integral with one another. The longitudinal axis 55 of proximal section 45 is offset from the longitudinal axis 60 of distal section 35 (e.g., at an approximately 12 degree angle). The length and diameters of distal section 35 and proximal section 45, and the degree of offset of the longitudinal axis 55 of proximal section 45 from the longitudinal axis 60 of distal section 35, are dependent on the size of the bone receiving intramedullary rod 10, such that intramedullary rod 10 may be deployed in an antegrade fashion down the intramedullary canal of the femur of a patient, with distal section 35 being disposed in the shaft of the femur and proximal section 45 being disposed in the proximal femur (e.g., in the trochanteric area). In one preferred form of the invention, proximal section 45 has a larger diameter than distal section 35. And in one preferred form of the invention, distal section 35 and proximal section 45 are both tapered, and their respective tapers are coordinated so as to form a substantially smooth taper across the length of intramedullary rod 10.

Preferably intramedullary rod 10 is hollow along its length, from distal end 40 to proximal end 50.

Distal section 35 comprises a static distal seat 65 for receiving distal interlocking screw 15 as distal interlocking screw 15 passes through a lateral portion of the femur, across distal section 35 of intramedullary rod 10 and into a medial portion of the femur (FIG. 1). To this end, static distal seat 65 comprises a round opening 70 on the lateral side of distal section 35 and a round opening 75 on the medial side of distal section 35. Round openings 70 and 75 are disposed on an axis 80 which preferably extends substantially perpendicular to the longitudinal axis 60 of distal section 35. In one preferred form of the invention, round openings 70 and 75 are of the same size, such that static distal seat 65 essentially comprises a cylindrical seat. Furthermore, round openings 70 and 75 are sized relative to distal interlocking screw 15 such that distal interlocking screw 15 will be unable to move relative to intramedullary rod 10 when distal interlocking screw 15 is disposed in static distal seat 65.

Proximal section 45 comprises a dynamic proximal seat 85 for receiving proximal interlocking screw 20 as proximal interlocking screw 20 passes through a lateral portion of the femur, across proximal section 45 of intramedullary rod 10 and into a medial portion of the femur (FIG. 1). To this end, dynamic proximal seat 85 comprises a slot opening 90 on the lateral side of proximal section 45 and a round opening 95 on the medial side of proximal section 45. Slot opening 90 is larger than round opening 95 in the proximal-to-distal direction, such that dynamic proximal seat 85 essentially comprises an offset frustorectangular seat. Furthermore, round opening 95 is sized relative to proximal interlocking screw 20, and slot opening 90 is sized relative to proximal interlocking screw 20, such that when proximal interlocking screw 20 is disposed in dynamic proximal seat 85, proximal interlocking screw 20 will be unable to move relative to round opening 95 but will be able to move relative to slot opening 90. The center of slot opening 90 and the center of round opening 95 are disposed on an axis 100 which is set at an angle of approximately 124-137 degrees to the longitudinal axis 55 of proximal section 45. The locus of fixation of proximal interlocking screw 20 with intramedullary rod 10 is via the medial round opening 95 in intramedullary rod 10. As will hereinafter be discussed, when proximal interlocking screw 20 is disposed in dynamic proximal seat 85, proximal interlocking screw 20 will initially reside in the proximal portion of slot opening 90 on the lateral side of intramedullary rod 10, and in round opening 95 on the medial side of the intramedullary rod. After load is applied (either by the surgeon to change the angle of proximal interlocking screw 20 with intramedullary rod 10 or when the patient weightbears), the bone will shift so that proximal interlocking screw 20 will thereafter reside in the distal portion of slot opening 90 on the lateral side of the intramedullary rod and in round opening 95 on the medial side of the intramedullary rod.

Distal Interlocking Screw

Figure 3:
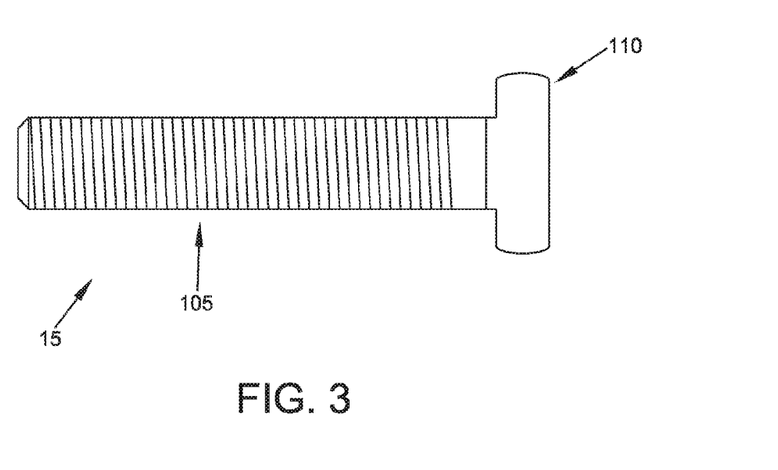
FIG. 3 is a schematic view showing the distal interlocking screw of the novel interlocking intramedullary rod assembly of FIG. 1.

Looking next at FIGS. 1 and 3, distal interlocking screw 15 is designed to be deployed in static distal seat 65 of distal section 35 of intramedullary rod 10. To this end, distal interlocking screw 15 comprises a threaded shaft 105 terminating in a head 110.

Proximal Interlocking Screw

Figure 4:
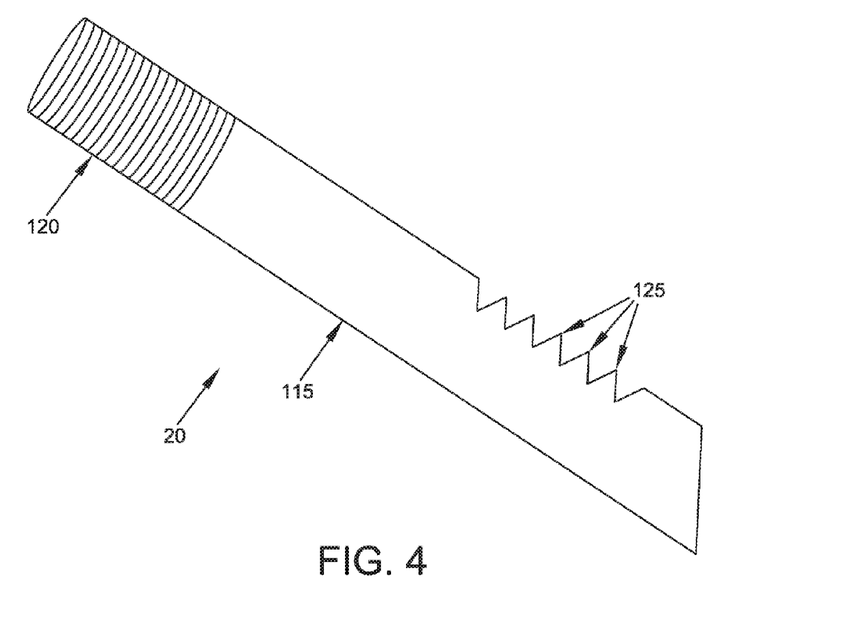
FIG. 4 is a schematic view showing the proximal interlocking screw of the novel interlocking intramedullary rod assembly of FIG. 1.

Looking next at FIGS. 1 and 4, proximal interlocking screw 20 is designed to be deployed in dynamic proximal seat 85 of proximal section 45 of intramedullary rod 10. To this end, proximal interlocking screw 20 comprises a shaft 115 having threads 120 on its distal end and ratchet teeth 125 on its proximal end.

If desired, proximal interlocking screw 20 may be hollow.

Locking Finger

As noted above, angular locking means are provided for locking proximal interlocking screw 20 relative to intramedullary rod 10, i.e., within dynamic proximal seat 85.

Figure 5:
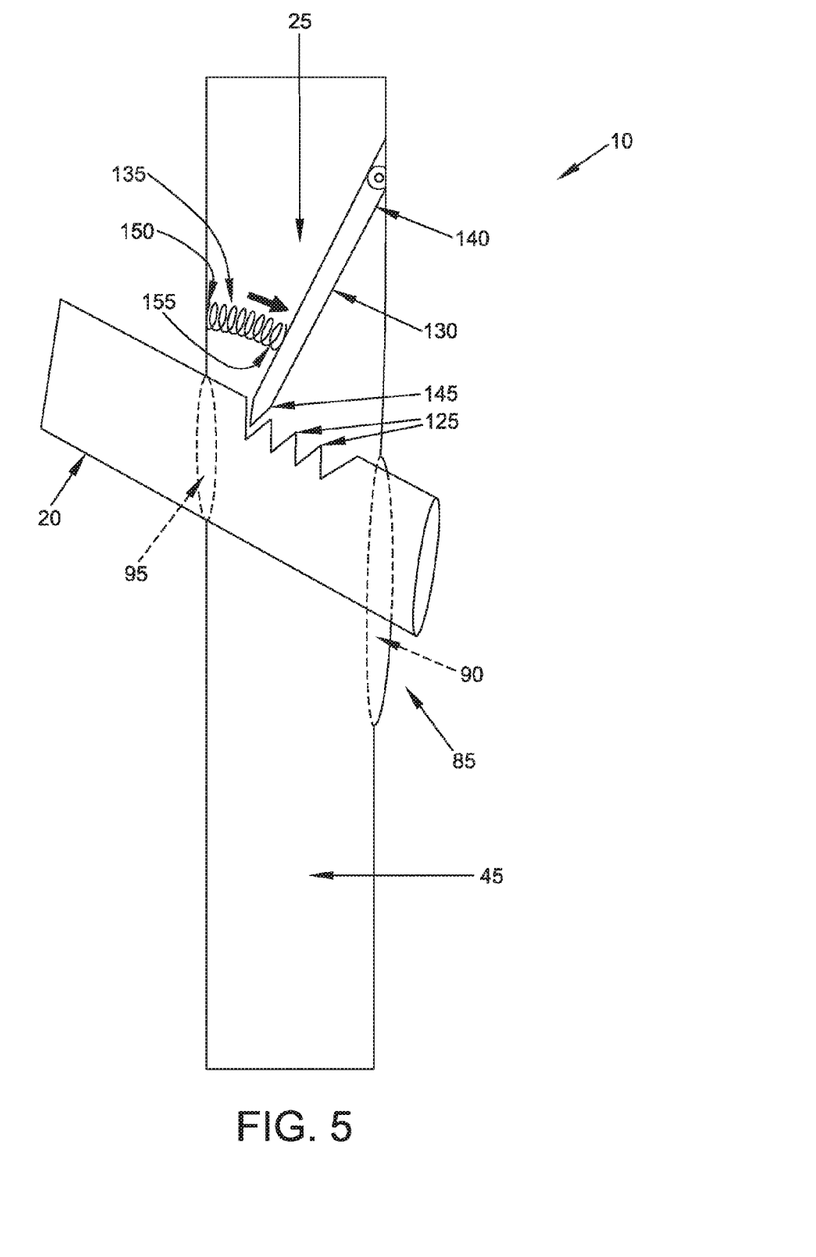
FIG. 5 is a schematic view showing the locking finger which comprises an exemplary embodiment of the angular locking means of the novel interlocking intramedullary rod assembly of FIG. 1.

To this end, and looking next at FIGS. 1 and 5, in one preferred form of the invention, a locking finger 25 is provided for engaging proximal interlocking screw 20 when proximal interlocking screw 20 is disposed in dynamic proximal seat 85. Locking finger 25 is mounted within proximal section 45 of intramedullary rod 10 and serves to engage proximal interlocking screw 20 as will hereinafter be discussed. Locking finger 25 allows for a specific kind of motion between proximal interlocking screw 20 and intramedullary rod 10 (and hence a specific kind of motion between the proximal end of the femur and the distal end of the femur).

More particularly, locking finger 25 generally comprises a lever 130 and a spring 135. One end 140 of lever 130 is pivotally mounted to the lateral side of intramedullary rod 10 (e.g., to the lateral side wall of proximal section 45) so as to allow for angular movement of lever 130 relative to intramedullary rod 10. The free end 145 of lever 130 engages the teeth 125 on proximal interlocking screw 20 with a one-way action as will hereinafter be discussed. This one-way action is the result of lever 130 being under constant lateral pressure from spring 135, as will also hereinafter be discussed.

Spring 135 is also mounted within proximal section 45 of intramedullary rod 10. One end 150 of spring 135 is mounted to the medial side of intramedullary rod 10 (e.g., to the medial side wall of proximal section 45), and the other end 155 of spring 135 is mounted to lever 135 so as to bias lever 135 laterally (i.e., counterclockwise from the angle of view of FIG. 5).

The Mechanism of Tension Banding Using Interlocking Intramedullary Rod Assembly

The mechanism of tension banding using interlocking intramedullary rod assembly 5 will now be discussed. For the purposes of example but not limitation, the mechanism of tension banding using interlocking intramedullary rod assembly 5 will be discussed in the context of a subtrochanteric fracture gap model, i.e., a 1 cm fracture gap 160 (FIG. 1) in the subtrochanteric area 165 of a femur 170.

First, intramedullary rod 10 is inserted into the fractured femur as shown in FIG. 1.

Second, proximal interlocking screw 20 is inserted, lateral-to-medial, through a lateral portion 175 of the femur, across dynamic proximal seat 85 in proximal section 45 of intramedullary rod 10 and then into the medial portion 180 of femur 170. Note that proximal interlocking screw 20 is inserted adjacent the proximal end of lateral slot opening 90 (FIGS. 1 and 5) and through medial round opening 95 until the threaded distal end 120 of proximal interlocking screw 20 is secured in the femoral head. As this occurs, the advancing proximal interlocking screw 20 engages lever 130 and forces the free end 145 of lever 130 medially, against the power of spring 135, with the free end 145 of lever 130 engaging teeth 125 formed in proximal interlocking screw 20. Note that teeth 125 prevent lever 130 from returning laterally under the power of spring 135.

Third, distal interlocking screw 15 is inserted, lateral-to-medial, through a lateral portion of the femur, across static distal seat 65 (FIG. 2) in distal section 35 and into a medial portion of the femur. Note that distal interlocking screw 15 is securely mounted to distal section 35 of intramedullary rod 10 (by virtue of the disposition of distal interlocking screw 15 in circular openings 70 and 75 of intramedullary rod 10) as well as to the lateral and medial portions of the femur.

At this point, interlocking intramedullary rod assembly 5 and femur 170 are in the positions shown in FIGS. 1 and 5.

Figure 6:
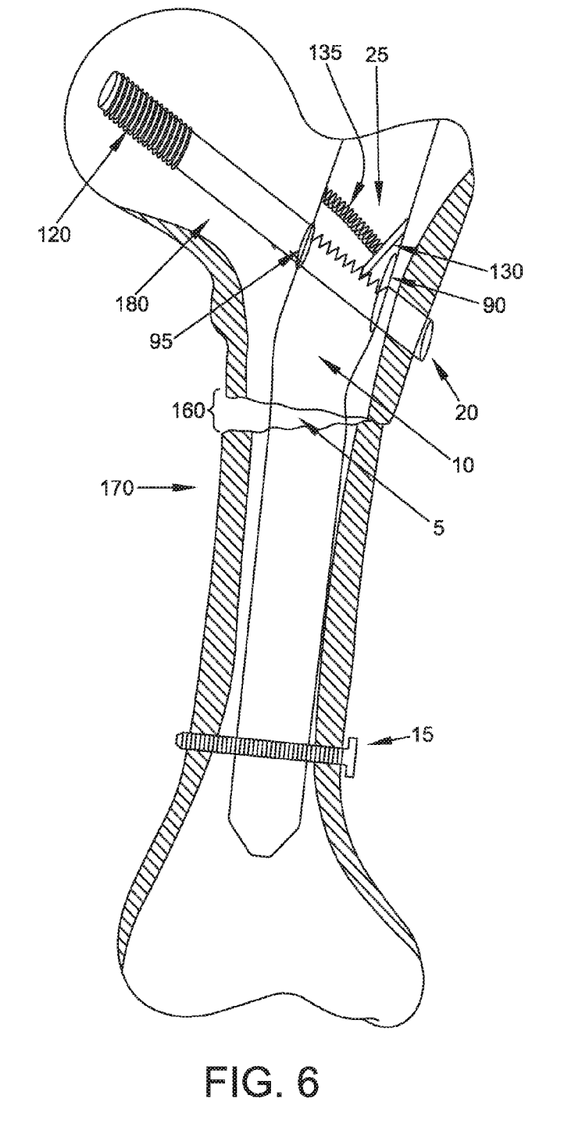
FIG. 6 is a schematic view like that of FIG. 1, except showing the interlocking intramedullary rod assembly and the fractured femur after partial reduction of the fracture.

Upon the application of force to the proximal end of the femur (e.g., by the surgeon during the procedure or upon the application of weight to the proximal end of the femur), the stress at the fracture site increases. Since the medial portion of dynamic proximal seat 85 is circular (i.e., round hole 95), the medial portion of dynamic proximal seat 85 acts as a static hole, preventing any kind of angular motion between proximal interlocking screw 20 and the medial wall of the femur. However, since the lateral portion of dynamic proximal seat 85 is a slot (i.e., slot opening 90), proximal interlocking screw 20 will slide inferiorly in lateral slot opening 90. This will create an angular collapse of the fracture site (FIG. 6). Significantly, as this angular collapse of the fracture site occurs, the free end 145 of lever 130 is moved counterclockwise (from the angle of view of FIG. 6) by spring 135. The free end 145 of lever 130 slides along the distally-moving teeth 125 of proximal interlocking screw 20 until, at the limit of the angular collapse, the free end of lever 130 lodges in teeth 125. Thereafter, when surgeon-applied force or weight-applied force is no longer applied to the proximal end of the femur, lever 130 and spring 135 prevent the bone from returning to its original fracture disposition, i.e., lever 130 and spring 135 cooperate with teeth 125 on proximal interlocking screw 20 to prevent any upward movement of proximal interlocking screw 20 within slot opening 90 on the lateral side of the femur.

Thus it will be seen that interlocking intramedullary rod assembly 5 creates a one-way angular collapse of the proximal fracture fragment into valgus, i.e., into an outward angulation of the 1 portion of the femur. The center of rotation of the proximal fracture fragment is through of the point where proximal interlocking screw 20 engages the medial round opening 95 of intramedullary rod 10. The valgus collapse of the fracture is accompanied by the following dynamic processes:

(i) valgus collapse—the medial fracture gap is maintained, the lateral fracture gap is decreased;

(ii) proximal interlocking screw 20 moves distally in slot opening 90 on the lateral side of intramedullary rod 10;

(iii) the position of lever 130 changes with respect to teeth 125, i.e., the disposition of lever 130 changes and engages different teeth as the result of the distal movement of the lateral end of proximal interlocking screw 20; and (iv) intramedullary rod 10 is medialized in the intramedullary canal of the femur.

Thus it will be seen that novel interlocking intramedullary rod assembly 5 combines the mechanical advantages of intramedullary rods with the mechanical advantages of tension banding, whereby to provide a device which is capable of treating all kinds of proximal femoral fractures (including not only subtrochanteric fractures and unstable intertrochanteric fractures, but also stable intertrochanteric fractures and other types of proximal femoral fractures), as well as treating fractures of other bones in the body.

Modifications of the Preferred Embodiments

Although the present invention has been described herein with reference to particular embodiments, it is to be understood that these embodiments are merely illustrative of the principles and applications of the present invention. It is, therefore, to be understood that numerous modifications may be made to the illustrative embodiments and that other arrangements may be devised without departing from the spirit and scope of the present invention. This devise and application of its components can be used for both proximal and distal fractures of the femur, tibia, and humerus.

What is claimed is:

1. A method for treating a fracture in the proximal femur, said method comprising:
   providing an interlocking intramedullary rod assembly comprising:
      an intramedullary rod comprising a distal section and a proximal section;
      a distal interlocking screw; and
      a proximal interlocking screw;
      wherein said distal section of said intramedullary rod comprises a static distal seat for receiving said distal interlocking screw, and said proximal section of said intramedullary rod comprises a dynamic proximal seat for receiving said proximal interlocking screw; and further wherein said static distal seat is configured to secure said distal interlocking screw to said intramedullary rod such that said distal interlocking screw cannot move relative to said intramedullary rod, and said dynamic proximal seat is configured to secure said proximal interlocking screw to said interlocking rod such that a first end of said proximal interlocking screw cannot move relative to said intramedullary rod and the second end of said proximal interlocking screw can move relative to said intramedullary rod;
   positioning said intramedullary rod in the intramedullary canal of the femur so that said distal section of said intramedullary rod resides within the shaft of the femur and said proximal section of said intramedullary rod resides within a proximal portion of the femur;
   inserting said proximal interlocking screw through the proximal portion of the femur, through said dynamic proximal seat and into the proximal portion of the femur, and inserting said distal interlocking screw through the shaft of the femur, through said static distal seat and into the shaft of the femur; and
   adjusting the disposition of said proximal interlocking screw within said dynamic proximal seat so as to at least partially reduce the fracture;
   further comprising a locking mechanism which restricts movement of said second end of said proximal interlocking screw to one-way movement relative to said intramedullary rod;
   wherein said one-way movement is distal movement relative to said intramedullary rod;
   wherein said distal movement of said second end of said proximal interlocking screw creates a one-way angular valgus collapse of the fracture.

2. A method according to claim 1 wherein said static distal seat comprises a first round opening and a second round opening.

3. A method according to claim 2 wherein said first round opening is disposed on a first side of said intramedullary rod and said second round opening is disposed on a second side of said intramedullary rod.

4. A method according to claim 3 wherein said first round opening is aligned with said second round opening along an axis which extends substantially perpendicular to the longitudinal axis of said distal section of said intramedullary rod.

5. A method according 2 wherein said distal interlocking screw comprises a shaft sized to make a tight fit within said first round opening and said second round opening.

6. A method according to claim 1 wherein said dynamic proximal seat comprises a round opening and a slot opening.

7. A method according to claim 6 wherein said round opening of said dynamic proximal seat is disposed on a first side of said intramedullary rod and said slot opening is disposed on a second side of said intramedullary rod.

8. A method according to claim 7 wherein said round opening of said dynamic proximal seat and the longitudinal center of said slot opening lie along an axis which extends at a non-perpendicular angle to the longitudinal axis of said proximal section said intramedullary rod.

9. A method according to claim 6 wherein said proximal interlocking screw comprises a shaft sized to make a tight fit within said round opening of said dynamic proximal seat and a sliding fit with said slot opening.

10. A method according to claim 1 wherein said locking mechanism is configured to selectively lock said second end of said proximal interlocking screw relative to said intramedullary rod after said second end of said proximal interlocking screw has moved relative said intramedullary rod.

11. A method according to claim 10 wherein said proximal interlocking screw comprises screw threads on a first end thereof and a plurality of teeth on a second end thereof, and further wherein said locking mechanism comprises a locking finger for selectively engaging said plurality of teeth so as to permit one-way movement of said second end of said proximal interlocking screw relative to said intramedullary rod.

12. A method according to claim 11 wherein said locking finger comprises a lever pivotally mounted to said intramedullary rod and a spring biasing said lever.

13. A method according to claim 1 wherein the disposition of said proximal interlocking screw can be changed relative to said intramedullary rod after insertion of said proximal interlocking screw into said dynamic proximal seat.

14. A method according to claim 13 wherein a surgeon can change the disposition of said proximal interlocking screw relative to said intramedullary rod.

15. A method according to claim 13 wherein the disposition of said proximal interlocking screw relative to said intramedullary rod can be changed upon the application of weight to the proximal femur.

16. A method according to claim 13 wherein the disposition of said proximal interlocking screw can be changed relative to said intramedullary rod after insertion of said proximal interlocking screw so as to accommodate the valgus collapse of the fracture in the bone.

17. A method according to claim 1 wherein the disposition of said proximal interlocking screw within said dynamic proximal seat is adjusted upon weight bearing.

18. A method according to claim 1 wherein said proximal portion of said intramedullary rod assumes a more medial position in the femoral intrameduallray canal after weight bearing.

* * * * *